United States Patent
Boggs et al.

(10) Patent No.: US 9,462,967 B2
(45) Date of Patent: Oct. 11, 2016

(54) CONDYLE AXIS LOCATOR

(71) Applicant: Zimmer, Inc., Warsaw, IN (US)

(72) Inventors: Tyler S. Boggs, Warsaw, IN (US); Jia Li, Warsaw, IN (US); David S. Hatfield, Warsaw, IN (US)

(73) Assignee: ZIMMER, INC., Warsaw, IN (US)

( * ) Notice: Subject to any disclaimer, the term of this patent is extended or adjusted under 35 U.S.C. 154(b) by 588 days.

(21) Appl. No.: 13/934,484

(22) Filed: Jul. 3, 2013

(65) Prior Publication Data
US 2014/0012273 A1 Jan. 9, 2014

Related U.S. Application Data

(60) Provisional application No. 61/668,747, filed on Jul. 6, 2012.

(51) Int. Cl.
*A61B 5/11* (2006.01)

(52) U.S. Cl.
CPC .................................. *A61B 5/1121* (2013.01)

(58) Field of Classification Search
CPC .. A61B 5/1121; A61B 5/107; A61B 5/1072; A61B 5/11; G01B 21/20
USPC .......................... 33/512, 520, 555.1; 606/102
See application file for complete search history.

(56) References Cited

U.S. PATENT DOCUMENTS

| 1,662,670 A * | 3/1928 | Harter ................... A61B 5/107 33/514 |
|---|---|---|
| 3,046,670 A * | 7/1962 | Wydra ...................... G01B 3/14 33/555.1 |
| D248,918 S * | 8/1978 | Kudo ........................... D11/241 |
| 4,963,152 A * | 10/1990 | Hofmann ................ A61F 2/389 623/20.31 |
| 4,978,351 A * | 12/1990 | Rozas ................ A61B 17/1725 606/102 |
| 5,070,623 A * | 12/1991 | Barnes .................... A61B 5/107 33/512 |
| 5,470,354 A * | 11/1995 | Hershberger .......... A61B 5/224 128/898 |
| 6,273,090 B1 * | 8/2001 | Nelson ................. A61B 5/4312 128/846 |
| 7,141,053 B2 * | 11/2006 | Rosa ..................... A61B 17/155 606/86 R |
| 7,632,238 B1 * | 12/2009 | Scarberry ............ A61B 5/1072 600/590 |
| 7,708,741 B1 * | 5/2010 | Bonutti .............. A61B 19/2203 128/898 |
| 8,070,752 B2 * | 12/2011 | Metzger ............... A61B 17/154 606/86 R |
| 8,377,066 B2 * | 2/2013 | Katrana ............... A61B 17/846 606/86 R |
| D725,774 S * | 3/2015 | Lubensky .................... D24/140 |
| 8,973,281 B1 * | 3/2015 | Fiquette ................. G01B 3/002 33/501.45 |
| 2003/0188446 A1 * | 10/2003 | Mellander ................ G01B 7/12 33/555.1 |

(Continued)

*Primary Examiner* — David Bates
(74) *Attorney, Agent, or Firm* — Schwegman Lundberg & Woessner, P.A.

(57) ABSTRACT

An apparatus and methods for locating the axis of rotation of one or more condyles are disclosed. A condyle axis locator can include a first concave member, a second concave member, and a handle extending between the first and second concave members. The first and second concave members can include first and second locating members, respectively, extending from a surface of the first and second concave members. The first and second locating members can each include at least one opening for receiving a marking instrument. A method for locating the axis of rotation of a condyle can include positioning a first longitudinal bone in flexion relative to an adjacent second longitudinal bone, placing one of the concave members of the condyle axis locator under the condyle, and inserting a marking instrument in the opening of the locating member to mark the axis of rotation of the condyle.

23 Claims, 4 Drawing Sheets

(56) References Cited

U.S. PATENT DOCUMENTS

| | | | | |
|---|---|---|---|---|
| 2005/0203541 A1* | 9/2005 | Steffensmeier | A61B 19/46 | 606/102 |
| 2005/0217130 A1* | 10/2005 | Danielli | B24B 49/045 | 33/555.1 |
| 2006/0184067 A1* | 8/2006 | Clark | A61B 5/107 | 600/587 |
| 2007/0227024 A1* | 10/2007 | Beaule | A61F 2/4657 | 33/512 |
| 2008/0289205 A1* | 11/2008 | Thierman | G01B 11/255 | 33/558.4 |
| 2012/0152017 A1* | 6/2012 | Stein | A61B 5/107 | 73/379.01 |
| 2013/0079787 A1* | 3/2013 | Spencer Jones | A61B 17/1767 | 606/96 |
| 2013/0310841 A1* | 11/2013 | Fitz | A61B 5/1072 | 606/102 |
| 2014/0182151 A1* | 7/2014 | Li | A45D 29/00 | 33/512 |
| 2014/0276240 A1* | 9/2014 | Stein | A61B 90/37 | 600/595 |
| 2015/0148653 A1* | 5/2015 | Fleig | A61B 5/1072 | 600/407 |

* cited by examiner

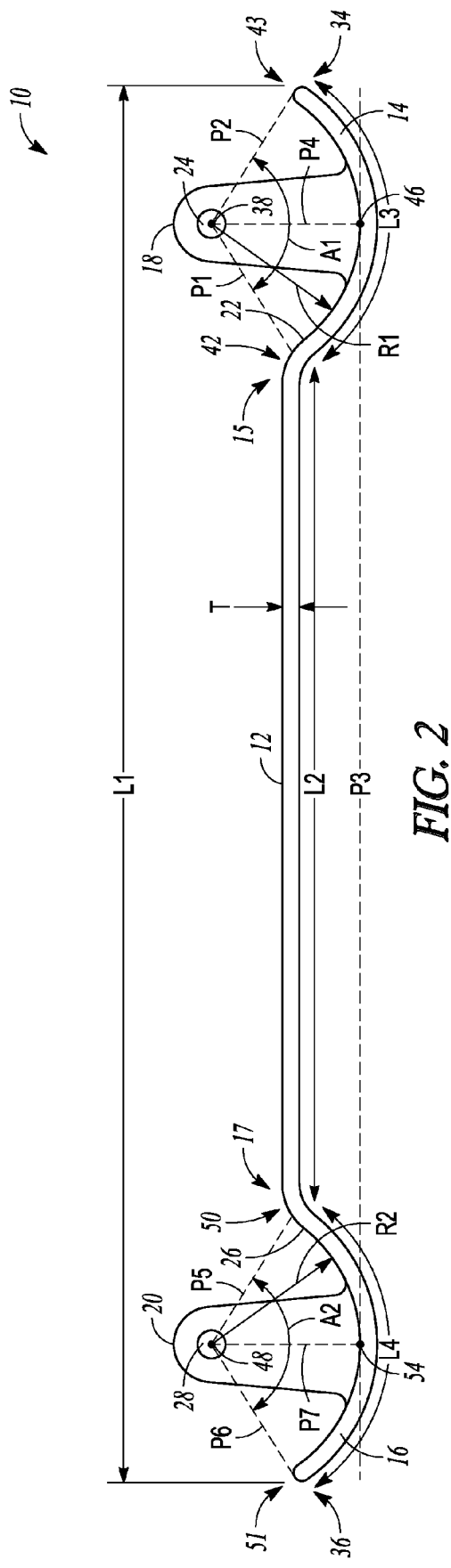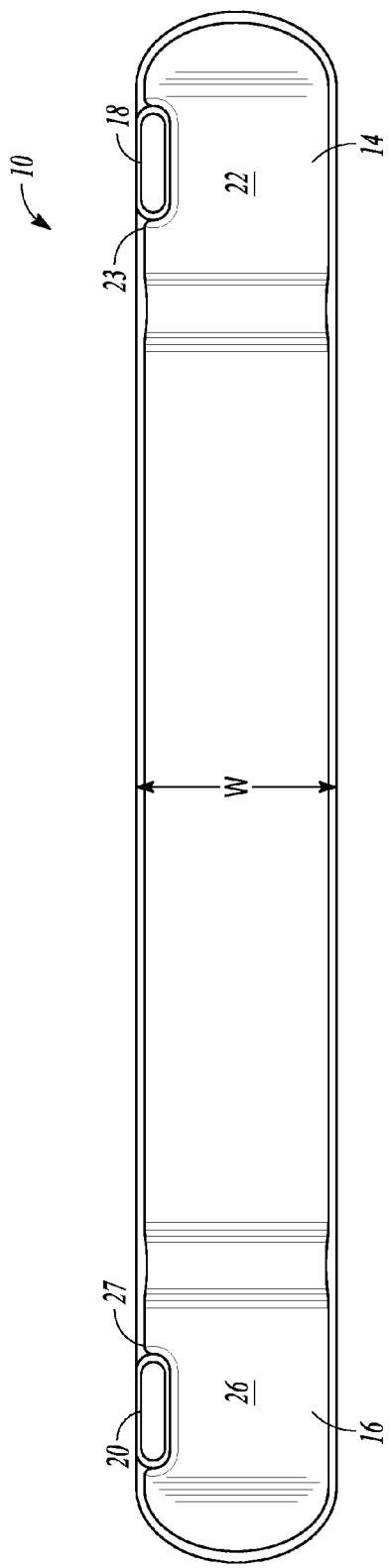
FIG. 2
FIG. 3

CONDYLE AXIS LOCATOR

CLAIM OF PRIORITY

This application claims the benefit of priority under 35 U.S.C. §119 of U.S. Provisional Patent Application Ser. No. 61/668,747, entitled "CONDYLE AXIS LOCATOR", and filed on Jul. 6, 2012, which is incorporated by reference herein in its entirety.

TECHNICAL FIELD

This patent document can relate to orthopedic procedures, and more particularly, to an apparatus and methods for locating and marking the axis of rotation of one or more condyles.

BACKGROUND

Orthopedic procedures for the replacement of all, or a portion of, a patient's joint have been developed over the last thirty years. Currently, the procedures used to prepare the bone and seat the implants are generally referred to as open procedures. For the purposes of this discussion, the term "open procedure" will refer to a procedure wherein an incision is made through the skin and underlying tissue to fully expose a large portion of the particular joint surface. After the initial incision in the skin, the internal wound can be enlarged to fully expose the areas to be prepared. With the wound enlarged, the clinician can perform various pre-surgical planning tasks prior to commencing a joint restoration procedure.

A preliminary step in knee arthroscopy, partial or total knee arthroplasty, femur replacement, and other knee or related orthopedic procedures can include the act of approximating and marking the axis of rotation of one or more condyles. In certain examples, locating and marking the axis of rotation can assist the clinician or surgeon as he or she compares the axis of rotation of the femur relative to the tibia, in order to determine, for example, the varus-valgus angle.

OVERVIEW

The present inventors recognize, among other things, a need for precisely locating and marking the axis of rotation of one or both posterior condyles of a femur during a knee orthopedic procedure. During knee arthroscopy or replacement procedures, for example, it is important to prevent potential errors resulting from inaccurately marking the condylar axis of rotation.

An apparatus and methods for locating the axis of rotation of posterior condyles of a femur are disclosed. A condyle axis locator can include a first concave member, a second concave member, and a handle extending between the first and second concave members. The first and second concave members can include first and second locating members, respectively, extending from a surface on the first and second concave members. The first and second locating members can include at least one opening for receiving a marking instrument.

A method for precisely locating the axis of rotation of a lateral condyle can include positioning a first longitudinal bone in flexion relative to an adjacent second longitudinal bone, placing a first concave member under the lateral condyle with the handle oriented generally parallel to an operating table or a floor supporting the operating table, and inserting a marking instrument in an opening of the first locating member to mark the axis of rotation of the lateral condyle. A method for precisely locating the axis of rotation of a medial condyle can similarly include positioning the first longitudinal bone in flexion relative to the adjacent second longitudinal bone, placing a second concave member under the medial condyle with the handle oriented generally parallel to the operating table or the floor supporting the operating table, and inserting a marking instrument in an opening of the second locating member to mark the axis of rotation of the medial condyle.

To better illustrate the apparatus and methods disclosed herein, a non-limiting list of examples is provided here:

In Example 1, a condyle axis locator comprises a first concave member, a second concave member, a handle extending between the first concave member and the second concave member, a first locating member extending from a surface of the first concave member and having a first opening, and a second locating member extending from a surface of the second concave member and having a second opening.

In Example 2, the condyle axis locator of Example 1 is optionally configured such that the first concave member includes a first radius extending from a top surface of the first concave member to a center of the first opening and the second concave member includes a second radius extending from a top surface of the second concave member to a center of the second opening.

In Example 3, the condyle axis locator of Example 2 is optionally configured such that the first radius is from about 1.65 centimeters to about 2.3 centimeters, and the second radius is from about 1.65 centimeters to about 2.3 centimeters.

In Example 4, the condyle axis locator of any one of Examples 1-3 is optionally configured such that the first concave member is defined by a first plane between a center of the first opening and an inside end of the first concave member, a second plane between a center of the first opening and an outside end of the first concave member, and an angle between the first plane and the second plane. The angle can be from about 90 to about 130 degrees.

In Example 5, the condyle axis locator of Example 4 is optionally configured such that the angle is about 110 degrees.

In Example 6, the condyle axis locator of any one of Examples 1-5 is optionally configured such that the second concave member is defined by a first plane between a center of the second opening and an inside end of the second concave member, a second plane between a center of the second opening and an outside end of the second concave member, and an angle between the first plane and the second plane. The angle can be from about 90 to about 130 degrees.

In Example 7, the condyle axis locator of Example 6 is optionally configured such that the angle is about 110 degrees.

In Example 8, the condyle axis locator of any one of Examples 1-7 is optionally configured such that the first and second concave members include an arc length from about 3.18 centimeters to about 4.57 centimeters.

In Example 9, the condyle axis locator of any one of Examples 1-8 is optionally configured such that the first and second locating members extend from an upper surface of the first and second concave members, respectively, and the first opening is in a plane at a midpoint on the first concave member, and the second opening is in a plane at a midpoint on the second concave member.

In Example 10, the condyle axis locator of any one of Examples 1-9 is optionally configured such that the first and second openings provide a location of the axis of rotation of lateral and medial condyles of a femur.

In Example 11, the condyle axis locator of any one of Examples 1-10 is optionally configured such that the first or second concave members are made from a material selected from stainless steel, titanium, chrome silicone, chrome vanadium, and plastic, and the first or second locating members are made from a material selected from stainless steel, titanium, chrome silicone, chrome vanadium, and plastic.

In Example 12, the condyle axis locator of any one of Examples 1-11 is optionally configured such that the handle is made from a material selected from the group consisting of stainless steel, titanium, chrome silicone, chrome vanadium, and plastic.

In Example 13, the condyle axis locator of any one of Examples 1-12 is optionally configured such that the first and second concave members are attached to first and second ends of the handle, respectively.

In Example 14, the condyle axis locator of any one of Examples 1-13 is optionally configured such that the first and second locating members are coupled to the first and second concave members, respectively.

In Example 15, a method of locating a condylar axis of rotation comprises positioning a first longitudinal bone in flexion relative to an adjacent second longitudinal bone, placing a first concave member of a condyle axis locator under a first condyle, marking a center point of an axis of rotation of the first condyle, placing a second concave member of the condyle axis locator under a second condyle, and marking a center point of an axis of rotation of the second condyle.

In Example 16, the method of Example 15 is optionally configured such that positioning the first longitudinal bone in flexion relative to the adjacent second longitudinal bone includes positioning a femur at or about a 90 degree angle relative to a tibia.

In Example 17, the method of any one of Examples 15 or 16 is optionally configured such that placing the first and second concave members under first and second condyles, respectively, includes maintaining a longitudinal handle connected to the first and second concave members in a substantially parallel orientation relative to an operating table or a floor supporting an operating table.

In Example 18, the method of any one of Examples 15-17 is optionally configured such that placing the first concave member under the first condyle includes positioning a first locating member extending from the first concave member adjacent to the axis of rotation of the first condyle.

In Example 19, the method of any one of Examples 15-18 is optionally configured such that marking the center point of the axis of rotation of the first condyle includes inserting a marking instrument through an opening on the first locating member.

In Example 20, the method of any one of Examples 15-19 is optionally configured such that placing the second concave member under the second condyle includes positioning a second locating member extending from the second concave member adjacent to the axis of rotation of the second condyle.

In Example 21, the method of any one of Examples 15-20 is optionally configured such that marking the center point of the axis of rotation of the second condyle includes inserting a marking instrument through an opening on the second locating member.

In Example 22, the method of any one of Examples 15-21 optionally further includes selecting the condyle axis locator from a plurality of locators having a plurality of first concave members of different sizes and a plurality of second concave members of different sizes In Example 23, the method of Example 22 is optionally configured such that selecting the condyle axis locator is based on a size of the first and second condyles.

In Example 24, the condyle axis locator or method of any one or any combination not Examples 1-23 is optionally configured such that all elements or options recited area available to use or selected from.

These and other examples and features of the present condyle axis locator apparatus and methods will be set forth in part in the following Detailed Description. This Overview is intended to provide non-limiting examples of the present subject matter—it is not intended to provide an exclusive or exhaustive explanation. The Detailed Description below is included to provide further information about the present condyle axis locator apparatus and methods.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2 is a side view of the condyle axis locator of FIG. 1.

FIG. 3 is a top view of the condyle axis locator of FIG. 1.

DETAILED DESCRIPTION

The present disclosure is directed to an apparatus and methods for locating and marking a center point of an axis of rotation of the posterior medial and lateral condyles of a femur. During a preliminary stage of a knee surgery, after making an incision in the knee joint to expose the bones comprising the joint, the surgeon can perform an analysis of the patient's knee joint, which can include determining the axis of rotation of the condyles. In accordance with the present application, a condyle axis locator can be used to more easily locate and mark an axis of rotation of the posterior condyles.

Figure 1:
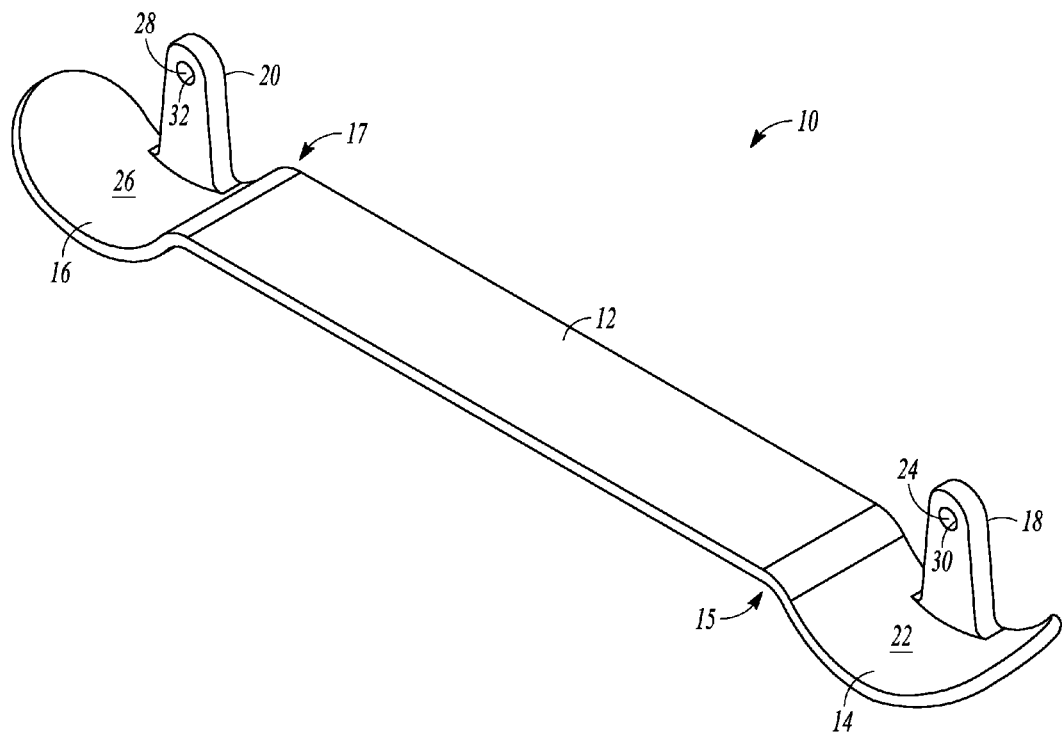
FIG. 1 is a perspective view of an example of a condyle axis locator in accordance with the present application.

FIG. 1 shows an example of a condyle axis locator 10 including a handle 12, a first concave member 14, a second concave member 16, a first locating member 18 and a second locating member 20. The handle 12 can be positioned between the first 14 and second 16 concave members and can include a first end 15 and a second end 17. The first locating member 18 can extend generally perpendicular from an upper surface 22 of the first concave member 14 and can include a first opening 24. Similarly, the second locating member 20 can extend generally perpendicular from an upper surface 26 of the second concave member 16 and can include a second opening 28. Although the first 18 and second 20 locating members are illustrated as including a single opening, additional openings can also be provided.

The condyle axis locator 10 can be used during a preliminary or initial step of a knee surgery, in order to determine an axis of rotation of the posterior condyles of the femur. Starting with the knee joint in flexion, a first 14 or second 16 concave member of the condyle axis locator 10 can be placed under a posterior condyle, either on a medial or a lateral side, depending on which leg is in being operated on. In certain examples, the femur can be flexed about 90 degrees relative to the tibia. The handle 12 can be positioned generally parallel to an operating table or to the floor. For example, if the first concave member 14 is placed under the medial condyle, the axis of rotation can be marked on the bone by placing a tip of a marking device through the opening 24. The second concave member 16 can then be placed under the lateral condyle, and the axis of rotation can be marked on the bone by placing the tip of the marking device through the opening 28.

The condyle axis locator 10 can be used on either leg. The concave member used on the medial side of the first leg can be configured for use as the concave member on the lateral side of the second leg, and the concave member used on the lateral side of the first leg can be configured for use as the concave member on the medial side of the second leg. The condyle axis locator 10 can be a single use device, or it can be used on multiple patients, provided it is sterilized after each use. The condyle axis locator 10 can be sized such that it can be easily handled by the user, while minimizing the thickness and overall dimension, so that the device is minimally invasive to the body.

As described in further detail below, the first 24 and second 28 openings can each be configured to receive at least a tip of a marking instrument. In use, when the first 14 and second 16 concave members are placed under the lateral and medial condyles of a femur, the first 24 and second 28 openings can be configured to generally align with the axis of rotation for the lateral and medial condyles. As illustrated in FIG. 1, each of the openings 24 and 28 can have a generally circular shape and can be enclosed around its perimeter by continuous inner wall surfaces 30 and 32, respectively. In some examples, the openings 24 and 28 can be open-ended by providing a discontinuity in the inner wall surfaces 30 and 32. Further, the openings 24 and 28 can have non-circular shapes such as, for example, ovals, squares, triangles, or the like. The openings 24 and 28 can be larger or smaller than those shown in FIG. 1, so long as the openings 24 and 28 can be used for receiving a marking instrument. In order to promote an accurate and consistent placement of the marking instrument on the bone, in certain examples, a size of the openings 24 and 28 can be minimized to help eliminate user variability during marking of the bone.

FIG. 2 is a side view of the condyle axis locator 10 of FIG. 1. The condyle axis locator 10 can include an overall thickness T, a total length L1 extending between a first end 34 and a second end 36 of the condyle axis locator 10, and a handle length L2 extending between a first end 15 and a second end 17 of the handle 12. The handle length L2 can vary and can be designed for ease of handling by the user. The total length L1 can be based on the handle length L2 in addition to a size of the first 14 and second 16 concave members.

With reference to the first concave member 14, a plane P1 can be defined between a center 38 of the first opening 24 and an inside end 42 of the first concave member 14, which can generally coincide with the first end 15 of the handle 12. A plane P2 can be defined between the center 38 of the first opening 24 and an outside end 43 of the first concave member 14, which can generally coincide with the first end 34 of the condyle axis locator 10. The planes P1 and P2 intersect at the center 38 of the first opening 24, forming a first angle A1 therebetween.

The first concave member 14 can include a first radius R1 extending from the center 38 of the opening 24 of the first locating member 18 to any point on the upper surface 22 of the first concave member 14 between the inside end 42 and the outside end 43. Because the first concave member 14 is a partial circle with a constant radius, the radius R1 can be defined in any plane extending between the center 38 of the opening 24 and a point lying along the upper surface 22 of the first concave member 14. The radius R1 is the reference point for locating the condylar axis of rotation when the first concave member 14 is placed under a condyle.

As illustrated in FIG. 2, in an example, the center 38 of the opening 24 of the first locating member 18 can be aligned with a lowermost point 46 of the arc formed between the inside end 42 and the outside end 43 of the first concave member 14. The lowermost point 46 can be, but is not necessarily, a midpoint of the arc. Particularly, the lowermost point 46 can lie in a plane P3 that is generally parallel to the plane containing the handle 12, and the center 38 of the opening 24 can lie in a plane P4 that is generally perpendicular to the plane P3 and that passes through the lowermost point 46. A length L3 can be defined as an arc length extending from the inside end 42 to the outside end 43 of the first concave member 14. The formula for calculating the arc length is:

$$\text{arc length} = \frac{2\pi RC}{360}, \quad (1)$$

where R is the radius of the arc (i.e., radius R1), and C is the central angle of the arc in degrees (i.e., the first angle A1).

Figure 4:
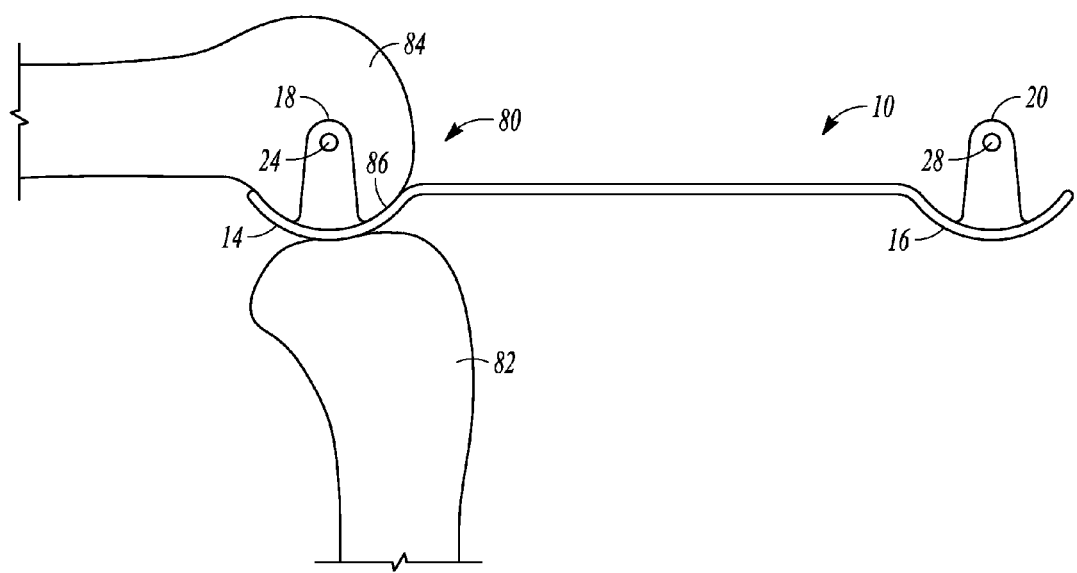
FIG. 4 is a side view of the condyle axis locator of FIG. 1 positioned adjacent to a femoral condyle and configured to determine the axis of rotation of the condyle.

The dimensions of the first concave member 14 facilitate placement of the first concave member 14 under a lateral or medial condyle of the femur. As shown in FIG. 4, which is described below, the first concave member 14 can be configured to cup the condyle without extending too far posteriorly relative to a shaft of the femur. As such, the first concave member 14 can have a relatively high radius of curvature. In an example, the arc length L3 can be determined based on a desired dimension of the radius R1. Because the arc length L3 is a function of the radius R1 as well as the central angle (C), a desired arc length L3 can also be achieved by modifying the locations of either or both of the inside end 42 and the outside end 43, thereby changing the central angle (C) in formula (1) above.

The first 14 and second 16 concave members can be essentially identical to one another in terms of design and dimensions; similarly, the first 18 and second 20 locating members can also be essentially identical to one another in terms of design and dimensions. This can facilitate use of the first 14 and second 16 concave members on both the medial condyle and the lateral condyle of either the right or left femur.

With reference to the second concave member 16, a plane P5 is defined between a center 48 of the second opening 28 and an inside end 50 of the second concave member 16, which can generally coincide with the second end 17 of the handle 12. A plane P6 can be defined between the center 48 of the second opening 28 and an outside end 51 of the second concave member 16, which can generally coincide with the second end 36 of the condyle axis locator 10. The planes P5 and P6 intersect at the center 48 of the second opening 28 forming a second angle A2 therebetween.

The second concave member 16 can include a second radius R2 extending from the center 48 of the opening 28 of the second locating member 20 to any point on the upper surface 26 of the second concave member 16 between the inside end 50 and the outside end 51. Because the second concave member 16 is a partial circle with a constant radius, the radius R2 can be defined in any plane extending between the center 48 of the opening 28 and a point lying along the upper surface 26 of the second concave member 16. The radius R2 is the reference point for locating the condylar axis of rotation when the second concave member 16 is placed under a condyle.

As illustrated in FIG. 2, in an example, the center 48 of the opening 28 of the second locating member 20 can be aligned with a lowermost point 54 of the arc formed between the inside end 50 and the outside end 51 of the second concave member 16. The lowermost point 54 can be, but is not necessarily, a midpoint of the arc. Particularly, the lowermost point 54 can lie in the plane P3 that is generally parallel to the plane containing the handle 12, and the center 48 of the opening 28 can lie in a plane P7 that is generally perpendicular to the plane P3 and that passes through the lowermost point 54. A length L4 is defined as an arc length extending from the inside end 50 of the second concave member 16 to the outside end 51 of the second concave member 16.

The dimensions of the second concave member 16 facilitate placement of the second concave member 16 under a lateral or medial condyle of the femur. As described above in reference to the first concave member 14, the arc length L4 is a function of the radius R2 and a location of the outside end 51, which changes the central angle (C) in formula (1) above. In an example, the arc length L4 can be determined based on a desired dimension of the radius R2. Because the arc length L4 is a function of the radius R2 as well as the central angle (C), a desired arc length L4 can also be achieved by modifying the locations of either or both of the inside end 50 and the outside end 51, thereby changing the central angle (C) in formula (1) above.

The first 18 and second 20 locating members are not restricted to the shape or sizes shown in the example condyle axis locator 10 of FIGS. 1-3. Rather, the first 18 and second 20 locating members can be designed with any suitable shape, size, or structural configuration that allows for alignment of at least one opening with a condylar axis of rotation, and that can receive a marking instrument. The first 18 and second 20 locating members can include at least one opening 24 and 28, respectively. A thickness of the first 18 or second 20 locating members can be more or less than the thickness T of the handle 12. Similarly, a thickness of the first 14 or second 16 concave members can be more or less than the thickness T of the locator 10. The thicknesses of the first 14 and second 16 concave members, the first 18 and second 20 locating members, and the handle 12 can be selected so as to minimize intrusion to the knee during surgery. In certain examples, the thickness T of the handle 12 can be from about 0.06 inches (about 0.15 centimeters) to about 0.1 inches (about 0.25 centimeters). In an example, the thickness T can be about 0.08 inches (about 0.2 centimeters).

In order to support a wide range of patient anatomies, in an example, a set of condyle axis locators 10 having the first 14 and second 16 concave members defined by various dimensions (e.g., radius, arc length) can be provided. The set of condyle axis locators 10 can also or alternatively include a plurality of handles 12 defined by various dimensions (e.g., length, thickness). The user can select the appropriately sized condyle axis locator 10 prior to the procedure, or alternatively, the user can intraoperatively position a plurality of different condyle axis locators 10 under the patient's condyle until the appropriately-sized locator for that patient is identified.

The following values for some of the dimensions of the condyle axis locator 10 are exemplary, and it is recognized that the condyle axis locator 10 described herein can have dimensions outside of the exemplary values provided herein. The first and second angles A1 and A2 of the first 14 and second 16 concave members, respectively, can be, in some examples, from about 90 degrees to about 130 degrees; in other examples, the first and second angles A1 and A2 can be from about 105 degrees to about 115 degrees. In an example, the first and second angles A1 and A2 can be about 110 degrees. The first radius R1 and the second radius R2 of the first 14 and second 16 concave members, respectively, can be, in some examples, from about 0.65 inches (about 1.65 centimeters) to about 0.9 inches (about 2.3 centimeters). In an example, the first radius R1 and the second radius R2 can be about 0.72 inches (about 1.83 centimeters); in another example, the first radius R1 and the second radius R2 can be about 0.75 inches (about 1.91 centimeters); in another example, the first radius R1 and the second radius R2 can be about 0.79 inches (about 2.0 centimeters); and in another example, the first radius R1 and the second radius R2 can be about 0.85 inches (about 2.16 centimeters).

In certain examples, the handle length L2 can be from about 3.5 inches (about 8.9 centimeters) to about 5.5 inches (about 14 centimeters). In an example, the handle length can be about 4 inches (about 10.2 centimeters). In certain examples, the overall length L1 of the condyle axis locator 10 can be from about 6 inches (about 15.2 centimeters) to about 8.5 inches (about 21.6 centimeters); in other examples, the overall length L1 can be from about 6.85 inches (about 17.4 centimeters) to about 7.15 inches (about 18.2 centimeters).

As described above, the arc lengths L3 and L4 of the first 14 and second 16 concave members, respectively, can be functions of the first radius R1 and the second radius R2, as well as the first and second angles A1 and A2 of the first 14 and second 16 concave members, respectively. In certain examples, the arc lengths L3 and L4 can be from about 1.25 inches (about 3.18 centimeters) to about 1.8 inches (about 4.57 centimeters); in other examples, the arc lengths L3 and L4 can be from about 1.35 inches (about 3.43 centimeters) to about 1.65 inches (about 4.19 centimeters). In an example, the arc lengths L3 and L4 can be about 1.38 inches (about 3.51 centimeters); in another example, the arc lengths L3 and L4 can be about 1.44 inches (about 3.66 centimeters); in another example, the arc lengths L3 and L4 can be about 1.52 inches (about 3.86 centimeters); and in another example, the arc lengths L3 and L4 can be about 1.63 inches (about 4.14 centimeters).

FIG. 3 is a top view of the condyle axis locator 10 of FIGS. 1 and 2. As shown in FIG. 3, the first 18 and second 20 locating members can be positioned on respective outer edges 23 and 27 of the first 14 and second 16 concave members. As further shown in FIG. 3, the condyle axis locator 10 can have an overall width, W. In certain examples, the width W can be from about 0.75 inches (about 1.91 centimeters) to about 1.0 inch (about 2.54 centimeters); in an example, the width W can be about 0.88 inches (about 2.24 centimeters). As shown in FIG. 3, the overall width W of the condyle axis locator 10 can be essentially the same from the first end 34 to the second end 36 of the locator 10. In other examples, the first concave member 14 and the second concave member 16 can each have a width different than a width of the handle 12. The width of the first 14 and second 16 concave members can be selected so as to sufficiently cup the condyle. As described above in reference to the thickness T, the width can be also selected so as to minimize intrusion to the bone and surrounding area during the procedure.

The condyle axis locator 10, or one or more components thereof, can be made from any suitable rigid or semi-rigid material. In certain examples, the condyle axis locator 10 or its components can be made from stainless steel, titanium, chrome silicone, chrome vanadium or plastic. The condyle axis locator 10 or its components can be manufactured using any suitable approach. In certain examples, such as if the condyle axis locator 10 or a component thereof is made from a metal, the locator 10 or the component can be stamped, punched, or formed from a sheet of metal. In other examples, the condyle axis locator 10 or a component thereof can be manufactured using molding, machining, cutting, forming, or through any other suitable manufacturing process.

In an example, the components of the condyle axis locator 10, including the handle 12, the first concave member 14, the second concave member 16, the first locating member 18, and the second locating member 20, can be manufactured as a single piece. Alternatively, the components can be manufactured separately and then attached together to form the condyle axis locator 10. In an example, the handle 12 can be attached to the first 14 and second 16 concave members using any suitable approach. By way of example, the handle 12 can be made from a different material than the first 14 and second 16 concave members, and can be attached, for example, by one or more welds. In another example, the handle 12 can be integral with the first 14 and second 16 concave members. In another example, the handle 12 can be detachably coupled to the first 14 and second 16 concave members using a suitable connection, such as a tongue and groove connection, a press-fit connection, a snap-fit connection, or combinations thereof.

The first 18 and second 20 locating members can be attached to the first 14 and second 16 concave members using any suitable approach. For example, if the first 18 and second 20 locating members are metal, they can be welded to the first 14 and second 16 concave member, or connected at a bend. In order to allow the condyle axis locator 10 to be used on both the medial and lateral condyles, as well as to be used interchangeably between the right and left legs, the first 14 and second 16 concave members can be attached to handle 12 in a similar manner and configuration. The first 18 and second 20 locating members can also be attached to the first 14 and second 16 concave members, respectively, in a similar manner and configuration.

In the example condyle axis locator 10 shown in FIGS. 1-3, the handle 12, the first 14 and second 16 concave members, and the first 18 and second 20 locating members can be formed as a singular piece. As described above, various sizes of locators 10 can be provided, and the user can select a particular locator 10 based in part on the anatomy of the patient. Alternatively, a modular condyle axis locator 10 can be provided that includes a handle 12 with a series of first 14 and second 16 concave members that can be selectively and detachably coupled thereto. The user can select the first 14 and second 16 concave members having the desired dimensions and attach the concave members to the handle 12 via a suitable connection means. In an example, the connection means can be a snap-fit connection, a press-fit connection, a threaded connection, or the like. Concave members 14 and 16 can be easily detachable so they can be quickly interchanged by a user during a procedure.

The first 24 and second 28 openings can be made using any suitable approach. For example, if the first 18 and second 20 locating members are metal, the openings 24 and 28 can be drilled or punched. The first 24 and second 28 openings can be sized using any suitable approach. For example, the first 24 and second 28 openings can be sized based on a tip size of a marking instrument.

FIG. 4 is a side view of the condyle axis locator 10 positioned within a knee joint 80 of a patient. As illustrated in FIG. 4, a first longitudinal bone 82 can be positioned in flexion relative to a second longitudinal bone 84. In an example, the first longitudinal bone 82 can be a tibia, and the second longitudinal bone 84 can be a femur. The second longitudinal bone 84 can include one or more condyles, such as lateral condyle 86. Specifically, FIG. 4 shows a right knee joint 80 with the first concave member 14 positioned under the lateral condyle 86 such that the axis of rotation of the lateral condyle 86 can be marked by inserting a marking instrument in the first opening 24 and marking the bone in a center of the opening 24. In some examples, the user can then insert a pin in the location of the marking to create an enlarged visual point representing the axis of rotation.

After the axis of rotation is marked on the lateral condyle 86, the second concave member 16 of the condyle axis locator 10 can be positioned under a medial condyle of the bone 82 (not shown). The second opening 28 can be used for marking the axis of rotation of the medial condyle. As similarly stated above, the user can insert a second pin where the marking is made through the opening 28.

As described above, the locator 10 can also be used on a left knee joint (not shown). In that case, the second concave member 16 can be placed under a lateral condyle to mark the axis of rotation of the lateral condyle. The first concave member 14 can be placed under a medial condyle to mark the axis of rotation of the medial condyle.

Figure 5:
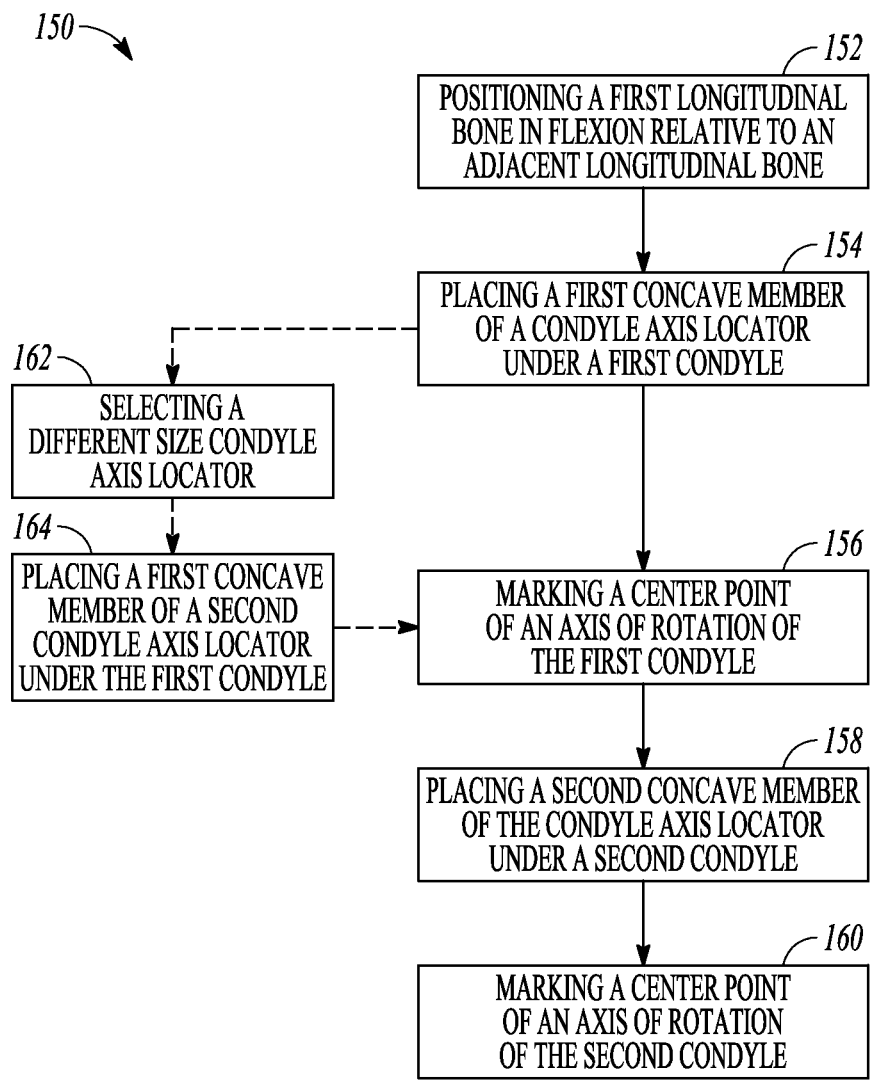
FIG. 5 is a process flowchart illustrating a method of using a condyle axis locator.

FIG. 5 illustrates a method 150 of using a condyle axis locator for locating and marking the axis of rotation of one or both posterior condyles of a bone using a condyle axis locator. At 152, a user (e.g., an orthopedic surgeon) can position a first longitudinal bone in flexion relative to an adjacent second longitudinal bone. In an example, the first longitudinal bone can be a tibia and the second longitudinal bone can be a femur.

At 154, the user can place a first concave member under a first condyle. At 156, the user can mark a center point of an axis of rotation of the first condyle, for example, by inserting a marking instrument through an opening of a first locating member. Particularly, when the first concave member is placed under the first condyle, the opening on the first locating member can be aligned such that marking the bone at a location aligned with the center of the opening coincides with the axis of rotation of the first condyle. At 158, the user can place a second concave member under a second condyle. At 160, the user can mark a center point of an axis of rotation of the second condyle. As described above with regard to marking of the axis of rotation of the first condyle, a marking instrument can be inserted through an opening in a second locating member.

As described above, condyle axis locators can be made in various sizes to support a wide range of patient anatomies. Thus the method 150 can include, in some examples, at 162, selecting a different size condyle axis locator. If the user determines in 154 that the first concave member does not fit the patient's first condyle, the user can choose a condyle axis locator having a larger or smaller first concave member. In that case, at 164, the user can place a first concave member of a second condyle axis locator under the first condyle. The user can repeat this "trial and error" process until an appropriately-sized first concave member is identified. When performing the procedure for locating and marking the condylar axis of rotation, the user can have several different condyle axis locators available such that finding the appropriately sized locator can be easily performed during the procedure. In certain examples, a condyle axis locator can have detachable concave members such that one handle can support different size concave members. In another example, the method 150 can include determining a size of a patient's condyle through other means, such as, for example, images taken prior to the procedure. In that example, the user can select the appropriately sized concave member prior to the procedure.

The present disclosure is focused on a condyle axis locator for use in locating and marking an axis of rotation of one or more condyles of the femur. However, it is recognized that the condyle axis locator can be configured for use in other areas of the body, particularly those involving a bone having a circular or semi-circular shape that can be cupped by the concave members of the locator. For example, the condyle axis locator can be configured for use in determining a center of a humeral head. Modifications can be made to the condyle axis locator, such as changing the size or shape of the concave members, to suit a particular application.

The above Detailed Description includes references to the accompanying drawings, which form a part of the Detailed Description. The drawings show, by way of illustration, specific embodiments in which the present locator apparatus and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim.

Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

What is claimed is:

1. A condyle axis locator, comprising:
   a first concave member;
   a second concave member;
   a handle extending between the first concave member and the second concave member;
   a first locating member extending from a surface of the first concave member and having a first opening; and
   a second locating member extending from a surface of the second concave member and having a second opening, wherein the first and second openings identify a location of the axis of rotation of lateral and medial condyles of a femur when one of the lateral and medial condyles of the femur is received by one of the first and the second concave members.

2. The condyle axis locator of claim 1, wherein the first concave member includes a first radius extending from a top surface of the first concave member to a center of the first opening and the second concave member includes a second radius extending from a top surface of the second concave member to a center of the second opening.

3. The condyle axis locator of claim 2, wherein the first radius is from about 1.65 centimeters to about 2.3 centimeters, and the second radius is from about 1.65 centimeters to about 2.3 centimeters.

4. The condyle axis locator of claim 1, wherein the first concave member is defined by:
   a first plane between a center of the first opening and an inside end of the first concave member;
   a second plane between a center of the first opening and an outside end of the first concave member; and
   an angle between the first plane and the second plane, wherein the angle is from about 90 to about 130 degrees.

5. The condyle axis locator of claim 4, wherein the angle is about 110 degrees.

6. The condyle axis locator of claim 1, wherein the second concave member comprises:
   a first plane between a center of the second opening and an inside end of the second concave member;
   a second plane between a center of the second opening and an outside end of the second concave member; and
   an angle between the first plane and the second plane, wherein the angle is from about 90 to about 130 degrees.

7. The condyle axis locator of claim 6 wherein the angle is about 110 degrees.

8. The condyle axis locator of claim 1, wherein the first and second concave members include an arc length from about 3.18 centimeters to about 4.57 centimeters.

9. The condyle axis locator of claim 1, wherein the first and second locating members extend from an upper surface of the first and second concave members, respectively, and the first opening is in a plane at a midpoint on the first concave member, and the second opening is in a plane at a midpoint on the second concave member.

10. The condyle axis locator of claim 1, wherein the first or second concave members are made from a material selected from stainless steel, titanium, chrome silicone, chrome vanadium, and plastic, and the first or second locating members are made from a material selected from stainless steel, titanium, chrome silicone, chrome vanadium, and plastic.

11. The condyle axis locator of claim 1, wherein the handle is made from a material selected from the group consisting of stainless steel, titanium, chrome silicone, chrome vanadium, and plastic.

12. The condyle axis locator of claim 1, wherein the first and second concave members are attached to first and second ends of the handle, respectively.

13. The condyle axis locator of claim 1, wherein the first and second locating members are coupled to the first and second concave members, respectively.

14. A condyle axis locator, comprising:
 a first concave member;
 a second concave member;
 a handle extending between the first concave member and the second concave member;
 a first locating member extending from a surface of the first concave member and having a first opening; and
 a second locating member extending from a surface of the second concave member and having a second opening;
 wherein the first concave member includes a first radius extending from a top surface of the first concave member to a center of the first opening and the second concave member includes a second radius extending from a top surface of the second concave member to a center of the second opening.

15. The condyle axis locator of claim 14, wherein the first radius is from about 1.65 centimeters to about 2.3 centimeters, and the second radius is from about 1.65 centimeters to about 2.3 centimeters.

16. The condyle axis locator of claim 14, wherein the first concave member is defined by:
 a first plane between a center of the first opening and an inside end of the first concave member;
 a second plane between a center of the first opening and an outside end of the first concave member; and
 an angle between the first plane and the second plane, wherein the angle is from about 90 to about 130 degrees.

17. The condyle axis locator of claim 16, wherein the angle is about 110 degrees.

18. A condyle axis locator, comprising:
 a first concave member;
 a second concave member;
 a handle extending between the first concave member and the second concave member;
 a first locating member extending from a surface of the first concave member and having a first opening; and
 a second locating member extending from a surface of the second concave member and having a second opening;
 wherein each of the first concave member and the second concave member has an upper surface configured to receive one of the lateral and medial condyles of the femur and the first and second locating members extend from the upper surface of the first and second concave members, respectively, and wherein the first opening is in a plane at a midpoint on the first concave member, and the second opening is in a plane at a midpoint on the second concave member.

19. The condyle axis locator of claim 18, wherein the first and second openings identify a location of the axis of rotation of lateral and medial condyles of a femur when one of the lateral and medial condyles of the femur is received by one of the first and the second concave members.

20. The condyle axis locator of claim 18, wherein the first concave member includes a first radius extending from a top surface of the first concave member to a center of the first opening and the second concave member includes a second radius extending from a top surface of the second concave member to a center of the second opening.

21. The condyle axis locator of claim 20, wherein the first radius is from about 1.65 centimeters to about 2.3 centimeters, and the second radius is from about 1.65 centimeters to about 2.3 centimeters.

22. The condyle axis locator of claim 18, wherein the first concave member is defined by:
 a first plane between a center of the first opening and an inside end of the first concave member;
 a second plane between a center of the first opening and an outside end of the first concave member; and
 an angle between the first plane and the second plane, wherein the angle is from about 90 to about 130 degrees.

23. The condyle axis locator of claim 18, wherein the angle is about 110 degrees.

* * * * *